US009309289B2

(12) United States Patent
Pinschewer et al.

(10) Patent No.: US 9,309,289 B2
(45) **Date of Patent: *Apr. 12, 2016**

(54) REPLICATION-DEFECTIVE ARENAVIRUS VECTORS

(71) Applicant: UNIVERSITAT ZURICH, Zurich (CH)

(72) Inventors: Daniel D. Pinschewer, Cologny (CH); Lukas Flatz, Schaan (LI); Andreas Bergthaler, Gmunden (AT); Rolf Zinkernagel, Zumikon (CH)

(73) Assignee: Universitat Zurich, Zurich (CH)

( * ) Notice: Subject to any disclaimer, the term of this patent is extended or adjusted under 35 U.S.C. 154(b) by 85 days.

This patent is subject to a terminal disclaimer.

(21) Appl. No.: 14/061,025

(22) Filed: Oct. 23, 2013

(65) Prior Publication Data

US 2014/0050760 A1 Feb. 20, 2014

Related U.S. Application Data

(63) Continuation of application No. 12/810,382, filed as application No. PCT/EP2008/010994 on Dec. 22, 2008, now Pat. No. 8,592,205.

(30) Foreign Application Priority Data

Dec. 27, 2007 (EP) .................................... 07025099

(51) Int. Cl.

*C12N 7/00* (2006.01)
*C12N 15/86* (2006.01)
*C07K 14/005* (2006.01)
*A61K 39/00* (2006.01)

(52) U.S. Cl.

CPC ................ *C07K 14/005* (2013.01); *C12N 7/00* (2013.01); *C12N 15/86* (2013.01); *A61K 2039/525* (2013.01); *A61K 2039/5256* (2013.01); *C12N 2760/10043* (2013.01); *C12N 2760/10061* (2013.01); *C12N 2830/008* (2013.01); *C12N 2840/203* (2013.01); *C12N 2840/206* (2013.01)

(58) Field of Classification Search

CPC .................. A61K 2039/5256; A61K 2039/64; C12N 2740/15043; C12N 2770/24234; C07K 14/005

See application file for complete search history.

(56) References Cited

U.S. PATENT DOCUMENTS

| | | | |
|---|---|---|---|
| 5,789,245 | A | 8/1998 | Dubensky, Jr. et al. |
| 2005/0123517 | A1 | 6/2005 | McCray et al. |
| 2009/0041725 | A1 | 2/2009 | Neubert et al. |

FOREIGN PATENT DOCUMENTS

| | | | |
|---|---|---|---|
| EP | 1156118 | A1 | 11/2001 |
| EP | 1012295 | B1 | 10/2004 |
| EP | 1608393 | B1 | 2/2012 |
| WO | WO 2005/061534 | A2 | 7/2005 |
| WO | WO 2006/053871 | A2 | 5/2006 |
| WO | WO 2006/084746 | A1 | 8/2006 |
| WO | WO 2012/093340 | A2 | 7/2012 |

OTHER PUBLICATIONS

Bergthaler, 2006, “Envelope exchange for the generation of live-attenuated arenavirus vaccines”, PLOS Pathogen; 2(6):501-512.

Bergthaler et al., 2007, “Contributions of the lymphocytic choriomeningitis virus glycoprotein and polymerase to strain-specific differences in murine liver pathogenicity”, J Gen Virol; 88(Pt 2):592-603.

Bitzer et al., 2003, “Sendai virus vectors as an emerging negative-strand RNA viral vector system”, The Journal of Gene Medicine; 5:543-553.

Buchmeier et al., eds., 2007, “Arenaviridae: the viruses and their replication”, Fields Virology; Philadelphia, PA, USA: Wolter Kluwer Lippincott Williams & Wilkins. 2:1791-1827.

Cornu et al., 2001, “RING finger Z protein of lymphocytic choriomeningitis virus (LCMV) inhibits transcription and RNA replication of an LCMV S-segment minigenome”, J Virol; 75(19):9415-9426.

Dudek et al., 2006, “Replication-defective viruses as vaccines and vaccine vectors”, Virology; 344:230-239.

Flatz et al., 2006, “Recovery of an arenavirus entirely from RNA polymerase I/II-driven cDNA”, Proc Natl Acad Sci USA; 103(12):4663-4668.

Flatz et al., 2010, “Development of replication-defective lymphocytic choriomeningitis virus vectors for the induction of potent CD8+ T cell immunity”, Nature Medicine; 16(3):339-345.

Hass et al., 2004, “Replicon system for lassa virus”, J Virol; 78(24):13793-13803.

Karkhanis et al., 2007, “Mucosal vaccine vectors: replication-competent versus replication-deficient poxviruses”, Current Pharmaceutical Designs; 13:2015-2023.

Kunz et al., 2005, “Novel antiviral strategies to combat human arenavirus infections”, Current Molecular Medicine, 5:735-751.

(Continued)

*Primary Examiner* — Bao Li
(74) *Attorney, Agent, or Firm* — Jones Day

(57) ABSTRACT

The invention relates to an infectious arenavirus particle that is engineered to contain a genome with the ability to amplify and express its genetic information in infected cells but unable to produce further infectious progeny particles in normal, not genetically engineered cells. One or more of the four arenavirus open reading frames glycoprotein (GP), nucleoprotein (NP), matrix protein Z and RNA-dependent RNA polymerase L are removed or mutated to prevent replication in normal cells but still allowing gene expression in arenavirus vector-infected cells, and foreign genes coding for an antigen or other protein of interest or nucleic acids modulating host gene expression are expressed under control of the arenavirus promoters, internal ribosome entry sites or under control of regulatory elements that can be read by the viral RNA-dependent RNA polymerase, cellular RNA polymerase I, RNA polymerase II or RNA polymerase III. The modified arenaviruses are useful as vaccines and therapeutic agents for a variety of diseases.

11 Claims, 6 Drawing Sheets

(56) References Cited

OTHER PUBLICATIONS

Lee et al., 2000, "NP and L proteins of lymphocytic choriomeningitis virus (LCMV) are sufficient for efficient transcription and replication of LCMV genomic RNA analogs", J Virol; 74(8):3470-3477.

Lee et al., 2002, "Identification of the lymphocytic choriomeningitis virus (LCMV) proteins required to rescue LCMV RNA analogs into LCMV-like particles", Journal of Virology; 76(12):6393-6397.

Liljeström et al., 2001, "Expression of proteins using Semliki Forest virus vectors", Current Protocols in Molecular Biology; Supplement 29(1994):16.20.1-16.20.16.

Lundstrom, 2002, "Alphavirus-based vaccines", Current Opinion in Molecular Therapeutics; 4(1):28-34.

Lundstrom, 2005, "Biology and application of alphaviruses in gene therapy", Gene Therapy; 12:S92-S97.

Merkler et al., 2006, "Viral déjà vu elicits organ-specific immune disease independent of reactivity to self", J Clin Invest; 116(5):1254-1263.

Mueller et al., 2007, "Viral targeting of fibroblastic reticular cells contributes to immunosuppression and persistence during chronic infection", Proc Natl Acad Sci USA; 104(39):15430-15435.

Perez et al., 2003, "The small RING finger protein Z drives arenavirus budding: implications for antiviral strategies", Proc Natl Acad Sci USA;100(22):12978-12983.

Perez et al., 2004, "Myristoylation of the RING finger Z protein is essential for arenavirus budding", J Virol; 78(20):11443-11448.

Pinschewer et al., 2003, "Recombinant lymphocytic choriomeningitis virus expressing vesicular stomatitis virus glycoprotein", Proc Natl Acad Sci USA; 100(13):7895-7900.

Pinschewer et al., 2003, "Role of the virus nucleoprotein in the regulation of lymphocytic choriomeningitis virus transcription and RNA replication", Journal of Virology; 77(6):3882-3887.

Pinschewer et al., 2004, "Kinetics of protective antibodies are determined by the viral surface antigen", J Clin Invest; 114(7):988-993.

Pinschewer et al., 2005, "Dual role of the lymphocytic choriomeningitis virus intergenic region in transcription termination and virus propagation", J Virol; 79(7):4519-4526.

Plotkin, 2008, "Determinants of Memory T cell Responses", Vaccines 5$^{th}$ Edition, Chapter 2, p. 30.

Plotkin, 2008, "Mumps vaccine", Vaccines 5$^{th}$ Edition, Chapter 20, p. 444.

Plotkin, 2008, "Rubella vaccine", Vaccines 5$^{th}$ Edition, Chapter 29, p. 745.

Polo et al., 2002, "Virus-based vectors for human vaccine applications", Drug Discovery Today; 7(13):719-727.

Querec et al., 2009, Systems biology approach predicts immunogenicity of the yellow fever vaccine in humans, Nature Immunolgy; 10(1):116-125.

Sánchez et al., 2006, "Rescue of the prototypic Arenavirus LCMV entirely from plasmid", Virology; 350:370-380.

Takeda et al., 2003, "Protective efficacy of an AIDS vaccine, a single DNA priming followed by a single booster with a recombinant replication-defective sendai virus vector, in a macaque AIDS model", Journal of Virology; 77(17):9710-9715.

Tibbetts et al., 2003, "Establishment and maintenance of gammaherpesvirus latency are independent of infective dose and route of infection", Journal of Virology; 77(13):7696-7701.

Watanabe et al., 2002, "Immunogenicity and protective efficacy of replication-incompetent influenza virus-like particles", Journal of Virology; 76(2):767-773.

Zinkernagel, 2002, "Immunity, immunopathology and vaccines against HIV?", Vaccine; 20:1913-1917.

Third Party Observation, dated May 17, 2013, in European Application No. 08868316.4 (European National Stage of PCT/EP2008/010994).

Abel et al., 2010, "The Novel Tuberculosis Vaccine, AERAS-402, Induces Robust and Polyfunctional CD4$^+$ and CD8$^+$ T Cells in Adults", Am J Respir Crit Care Med; 181:1407-1417.

Loera-Arias et al., 2009, Targeting and Retention of HPV16 E7 to the Endoplasmic Reticulum Enhances Immune Tumour Protection, J. Cell. Mol; 14(4):890-894.

A

B

C

REPLICATION-DEFECTIVE ARENAVIRUS VECTORS

This application is a continuation of U.S. application Ser. No. 12/810,382, filed Aug. 3, 2010, which is a national stage of International Application No. PCT/EP2008/010994 filed Dec. 22, 2008, which claims the benefit of priority of European Application No. 07025099.8 filed Dec. 27, 2007, each of which is incorporated by reference herein in its entirety.

FIELD OF THE INVENTION

The invention relates to genetically modified arenaviruses suitable as vaccines or gene therapy vectors, and to methods of using these in vaccination and treatment of diseases.

BACKGROUND OF THE INVENTION

Preventive vaccines represent one of the most successful chapters of modern medicine, having led to the worldwide eradication of smallpox and to the control of polio, measles and many other devastating infectious diseases. More recently, vaccines have become available that prevent cancer, and strong efforts are ongoing to exploit "vaccines" in a therapeutic fashion, raising hope for both infection and malignancy. Historically, vaccination strategies have comprised a variety of approaches: Starting with the use of wild type infectious agents and the auto-(re)-inoculation of tumor cells, followed by live-attenuated agents and killed tumor tissues, clinical medicine has over time moved more and more to the use of (inert) proteins and/or other extracts (commonly referred to as "antigen") derived from infectious agents or tumors, respectively. This gradual process represents the search for safer vaccine formulation, often accompanied, however, by a relative loss in efficacy. In recent years the advancement of biological engineering has made possible yet an additional approach that currently is widely considered among the most promising ones: infectious agents serving as a "ferry" (called "vector") are equipped with an antigen from the pathogen or tumor of choice. Thereby, the immune response of the vaccine recipient recognizes the antigen of interest in the context of a strongly immune-enhancing ("immunogenic") context conferred by the vector.

The "vector approach" has also made possible the directed introduction of foreign genes into living cells at the level of tissue culture but also in multicellular organisms including man, and vectors can therefore also be exploited for the expression of genes in cultured cells or in gene therapy.

A variety of vectors are currently in experimental use, both for vaccination and gene therapy, with the ultimate goal of optimizing efficacy and safety for clinical application (vaccinology and gene therapy) or for biotechnology (gene transfer in cell culture).

As a common observation, vectors tend to share general traits of the organism, e.g. virus, they are derived from. The exploitation of a novel family of viruses for vector design promises therefore a novel combination of traits that may confer this new type of vector with unprecedented capabilities and corresponding applications in biomedical application. Vector design needs, however, to take into account the safety profile of the organism used, and must come up with a strategy of how to eliminate the organism's pathogenic potential in a manner that does not interfere with desirable traits such as immunogenicity for administration as a vaccine.

Arenaviruses in general and lymphocytic choriomeningitis virus (LCMV) in particular have been known for more than seventy years to elicit extraordinarily strong and long-tasting humoral and cell-mediated immune responses. Of note, though, protective neutralizing antibody immunity against the viral envelope glycoprotein (GP) is minimal, meaning that infection results in minimal antibody-mediated protection against re-infection if any. Also it has been firmly established for decades that owing to their non-cytolytic (not cell-destroying) nature, arenaviruses can, under certain conditions, maintain long-term antigen expression in animals without eliciting disease. Recently, reverse genetic systems for the manipulation of the infectious arenavirus genome (L. Flatz, A. Bergthaler, J. C. de la Torre, and D. D. Pinschewer, Proc Natl Acad Sci USA 103:4663-4668, 2005; A. B. Sanchez and J. C. de la Torre, Virology 350:370, 2006) have been described, but arenaviruses have not so far been exploited as vaccine vectors. Two major obstacles are mainly responsible: i) Arenaviruses can cause overwhelming infection which then can result in serious disease and immunosuppression. ii) The incorporation of foreign antigens of choice has not been possible.

SUMMARY OF THE INVENTION

The invention relates to an infectious arenavirus particle that is engineered to contain a genome with the ability to amplify and express its genetic information in infected cells but unable to produce further infectious progeny particles in normal, not genetically engineered cells.

More specifically the invention relates to such arenavirus particles comprising additional ribonucleic acids coding for proteins of interest or modulating host gene expression.

An arenavirus of the invention comprises a modified genome, wherein i) one or more of the four arenavirus open reading frames glycoprotein (GP), nucleoprotein (NP), matrix protein Z and RNA-dependent RNA polymerase L are removed or mutated to prevent propagation of infectivity in normal cells but still allowing gene expression in such cells;

ii) foreign ribonucleic acids coding for one or more proteins or modulating host gene expression are introduced and are transcribed from one or more of the four arenavirus promoters 5' UTR and 3' UTR of the S segment, and 5' UTR and 3' UTR of the L segment, or from additionally introduced promoters that can be read by the viral RNA-dependent RNA polymerase, by cellular RNA polymerase I, RNA polymerase II or RNA polymerase III, respectively, and wherein ribonucleic acids coding for proteins or modulating host gene expression are transcribed either by themselves or as read-through by fusion to arenavirus protein open reading frames; and optionally iii) one or more internal ribosome entry sites are introduced in the viral transcript sequence to enhance expression of proteins in the arenavirus-infected cell.

The invention furthermore relates to vaccines and pharmaceutical preparations comprising such genetically engineered arenaviruses, and to methods of vaccination and gene therapy using these genetically engineered arenaviruses.

The invention furthermore relates to expression of a protein of interest in a cell culture or to modulation of gene expression in cell culture wherein the cell culture is infected with genetically engineered arenaviruses.

Figure 1:
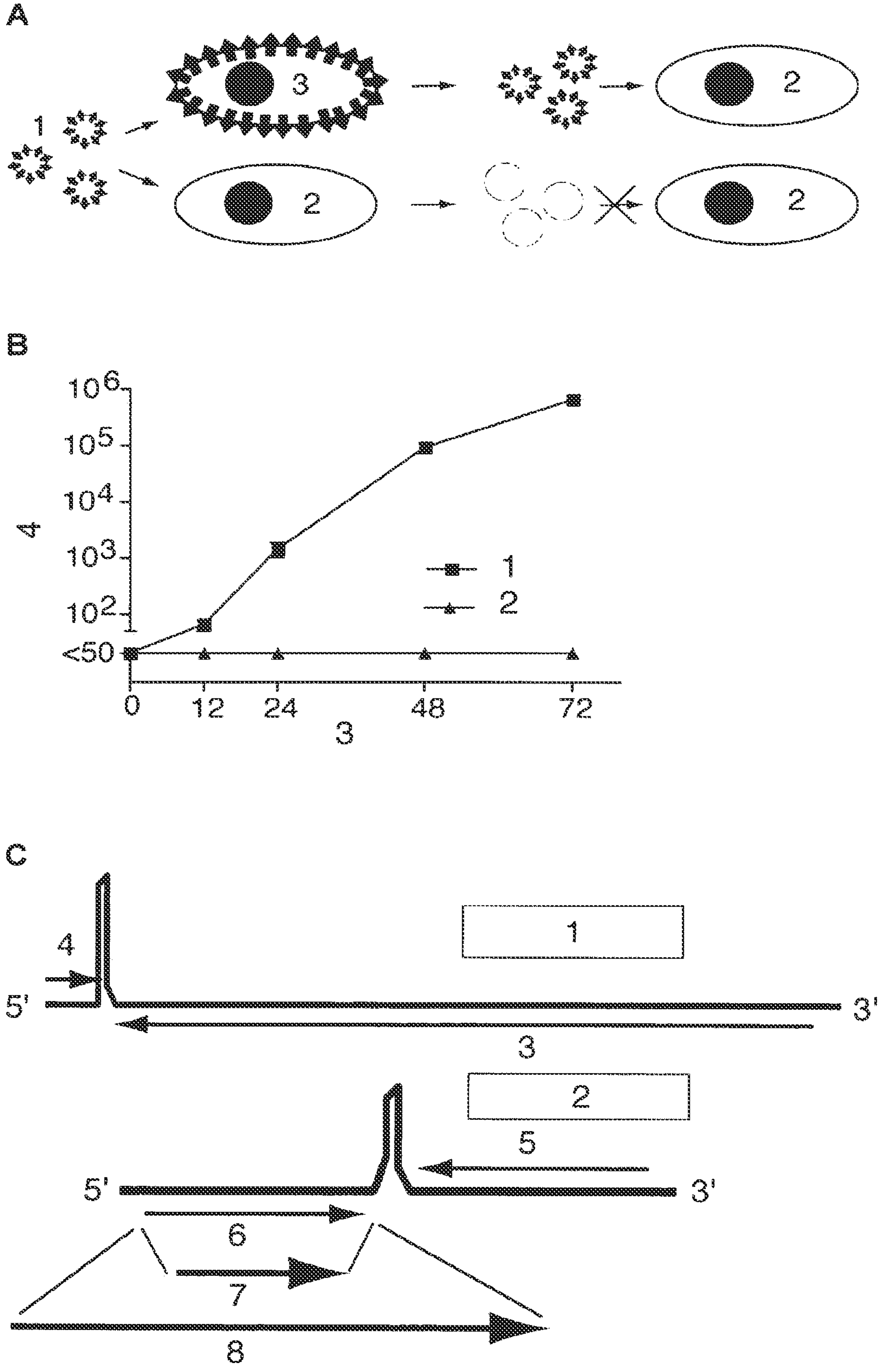
FIG. 1

Owing to the changes made to the type arenavirus genome, the derived arenavirus vectors replicate only in complementing cells.

A: Arenavirus vectors (1) can infect both normal cells (2) or complementing cells (C-cells, 3). Upon infection of cells further infectious vector progeny are formed whereas infection of normal cells yields either no vector particles or non-infectious ones.

B: C-cells (1) and normal cells (2) were infected with an LCMV-based vector (rLCMV/GFP) expressing green fluorescent protein (GFP) instead of LCMV-GP, and samples of supernatant collected at various time points (3, given in hours). Infectivity the supernatant (4, given PFU/ml) was determined in a focus forming assay.

C: The wild type arenavirus genome consists of a large (L; 1) and a small (S; 2) segment. The L segment expresses the L (3) and Z (4) genes, whereas the S segment carries the NP (5) and GP (6) genes. One strategy to generate a replication-deficient arenavirus vector can be to substitute the GP gene for genes of interest, for example GFP (7) or ovalbumin (OVA; 8).

FIG. 2

Schematic organization of complementing plasmid (C-plasmid), of plasmids for intracellular expression of trans-acting factors (TF-plasmids) and of plasmids for intracellular expression of arenavirus vector genome segments (GS-plasmids).

A: example of a C-plasmid.

B: examples of TF-plasmids expressing the viral NP and L protein, respectively.

C: examples of GS-plasmids expressing the arenavirus vector S and L segments, respectively.

1: polymerase II promoter; 2: viral gene to be expressed for complementation; 3: internal ribosome entry site; 4: mammalian selection marker, such as puromycin resistance gene; 5: polyadenylation signal; 6: ampicillin resistance cassette; 7: origin of replication; 8: viral trans-acting factor, e.g. NP ORF; 9: viral trans-acting factor, e.g. L ORF; 10: promoter driving expression of arenavirus genome segment in C-cells, e.g. polymerase I promoter; 11: 5' UTR of the S segment; 12: antigen of interest; 13: IGR of the S segment; 14: NP gene; 15: 3' UTR of the S segment; 16: polymerase I terminator; 17: 5'UTR of the L segment; 18: Z gene; 19: IGR of the L segment; 20: L gene; 21: 3'UTR of the L segment.

FIG. 3

Arenavirus vectors are cleared within days after inoculation, and accordingly do not cause immunosuppression in vaccine recipients.

A: On day 0, mice were immunized intravenously with rLCMV/GFP (1). At different time points thereafter (2; given in days), viral genome copies (3, given in log 10) were measured in spleen.

B: As primary immunization/infection (1°), mice were either immunized with rLDMV/OVA (5) or were left uninfected (6) or were infected with LCMV wild type (7). On day 20, all mice were given an intraperitoneal infection (2) with vesicular stomatitis virus (VSV, 8). Subsequently, blood was collected for measuring antiviral and anti-vector T cell responses (3) and antiviral antibody responses (4). On day 28, H-2K$^b$-SIINFEKL (ovalbumin-derived CD8+ T cell epitope) specific CD8+ cells (9) and H-2K$^b$-VSV-NP52-29 (VSV-NP-derived CD8+ T cell epitope) specific CD8+ cells (10) were measured in peripheral blood by intracellular staining for interferon gamma upon peptide restimulation (values indicate the percentage of specific cells amongst CD8+ T cells). On day 27 (indicated as "d7" referring to the time point after VSV infection), day 29 (indicated as "d9") and day 61 (indicated as "d41"), serum was tested for total VSV neutralizing antibodies (11) and for beta-mercapto-ethanol-resistant IgS (12) in a 50% plaque reduction assay (values given as −log 2 of 40-fold prediluted serum).

FIG. 4

Arenavirus vectors elicit high frequencies of long-lived memory CD8+ T cells and long-lived antibody memory at high titers.

A. Mice were immunized rLCMV/OVA and blood samples were deflected over time (2; given in days) for measuring the frequency of H2K$^b$-OVA/SIINFEKL specific CD8+ T cells using MHC class I tetramers (3, values indicate the frequency of tetramer-positive CD8+ T cells within the CD8+ T cell compartment).

B: Mice were immunized with rLCMV/OVA at the indicated dose (1), either via the subcutaneous (s.c.) or intravenous (i.v.) route, and OVA-specific IgG in the serum was measured by ELISA on day 14 (5) and day 58 (6). Values are expressed as the dilution serum yielding twice background optical density (OD) measurements.

FIG. 5

Arenavirus vectors do not cause central nervous system disease

Mice were inoculated intracerebrally with rLCMV/OVA (open squares) or with wild type LCMV (closed circles), and were monitored at the indicated time points (1, indicated in days) for clinical signs of terminal choriomeningitis. For each time point, the number of healthy animals per number of animals tested (2) is displayed.

FIG. 6

Arenavirus vectors confer T cell and antibody-mediated protection against infectious challenge.

A) On day 0 of the experiment, mice were vaccinated using either rLCMV/OVA (group AA) or using a rLCMV control vector expressing the irrelevant Cre recombinase antigen as negative control (group BB). Intravenous challenge with recombinant *Listeria monocytogenes* expressing OVA was performed after an interval of either 16 or 58 days (d16, d58). Four days after challenge bacterial titers (1) were measured in the spleen of the animals (displayed in $\log_{10}$ colony forming units per organ). Black circles indicate values of individual mice. Vertical lines indicate the mean value of each group.

B) Type 1 interferon receptor-deficient mice were vaccinated (closed squares) with a LCMV vector that expresses an antigenic but non-functional variant of the vesicular stomatitis virus envelope protein G (modified by insertion of a foreign peptide sequence in its ectodomain) or were left without vaccination (open circles). One month later, all animals were challenged intravenously with $2\times10^6$ PFU vesicular stomatitis virus. At the in time points after challenge (2, indicated in days), the animals were monitored for clinical signs of terminal myeloencephalitis. For each time point and group, healthy survival is indicated as the number of healthy animals per number of animals tested (3).

DETAILED DESCRIPTION OF THE INVENTION

The invention relates to infectious arenavirus particles, referred to as arenavirus vectors, that are engineered to contain a genome with the ability to amplify and express its genetic information in infected cells but unable to produce further infectious progeny particles in normal, not genetically engineered cells. This principle is shown schematically in FIG. 1A. Example data are presented in FIG. 1B.

Replication of arenavirus vectors requires genetically engineered cells complementing the replication-deficient vector. Upon infection of a cell, the arenavirus vector genome expresses not only arenavirus proteins but also additional proteins of interest, for example antigens of interest. Arenavirus vectors are produced by standard reverse genetic techniques as described for LCMV (L. Flatz, A. Bergthaler, J. C. de la Torre, and D. D. Pinschewer, Proc Natl Acad USA 103:4663-4668, 2006; A. B. Sanchez and J. C. de la Torre, Virology 350:370, 2006), but their genome is modified in one or more of the following ways, resulting in the above-mentioned characteristics:

i) One or more, e.g. two, three or four, of the four arenavirus open reading frames (glycoprotein (GP); nucleoprotein (NP); the matrix protein Z; the RNA-dependent RNA polymerase L) are removed or mutated to prevent formation of infectious particles in normal cells albeit still allowing gene expression in arenavirus vector-infected cells.

ii) Foreign nucleic acids coding for one or more proteins can be introduced. Alternatively or in addition, foreign nucleic acids may be incorporated for modulating host gene expression. These include but are not limited to short hairpin RNAs (shRNA), small interfering RNA (siRNA), micro RNAs (miRNA), and precursors thereof. These foreign nucleic acids are transcribed from one or more, e.g. two or three of the four arenavirus promoters 5' UTR and 3' UTR of the S segment, and 5' UTR and 3' UTR of the L segment, or from additionally introduced promoter sequences that can be read by the viral RNA-dependent RNA polymerase, by cellular RNA polymerase I, RNA polymerase II or RNA polymerase III, such as duplications of viral promoter sequences that are naturally found in the viral UTRs, the 28S ribosomal RNA promoter, the beta actin promoter or the 5S ribosomal RNA promoter, respectively. The ribonucleic acids coding for proteins modulating host gene expression are transcribed and translated either by themselves or as read-through by fusion to arenavirus protein open reading frames, and expression of proteins in the host cell may be enhanced by introducing in the viral transcript sequence at the appropriate place(s) one or more, e.g. two, three or four, internal ribosome entry sites.

"Modulating host gene expression" as understood herein refers to reduction of expression of host genes or the enhancement thereof, either in all vector-targeted cells or in a cell type-specific manner. The desirable features can be achieved by adapting the nucleic acid sequence incorporated into vectors.

Arenavirus vectors can be used to improve life and health in general, and to immunize (in a preventive manner) or treat (in an immunotherapeutic manner) animals including men in a variety of contexts including but not limited to i) infections including but not limited to viruses such as human immunodeficiency virus (HIV), hepatitis B virus (HBV), hepatitis C virus (HCV), influenza viruses, and respiratory syncytial virus (RSV), bacteria such as mycobacteria, *haemophilus* spp., and *pneumococcus* spp., and parasites such as plasmodia, amebia, and philaria, and prions such as the infectious agents causing classical and variant Creutzfeldt-Jakob disease and ret cow disease;

ii) autoimmune diseases including but not limited to type I diabetes, multiple sclerosis, rheumatoid arthritis, lupus erythematosus, and psoriasis;

iii) neoplastic diseases including but not limited to melanoma, prostate carcinoma, breast carcinoma, lung carcinoma and neuroblastoma;

iv) metabolic diseases including but not limited to type II diabetes, obesity, and gout;

v) degenerative diseases including but not limited to Alzheimer's disease, and Parkinson's disease;

vi) inherited diseases including but not limited to Huntington's disease, severe combined immunodeficiency, and lipid storage diseases;

vii) substance dependencies including but not limited to tobacco and alcohol abuse; and viii) allergic diseases including but not limited to seasonal or perennial rhinoconjunctivitis, asthma and eczema.

Figure 3:
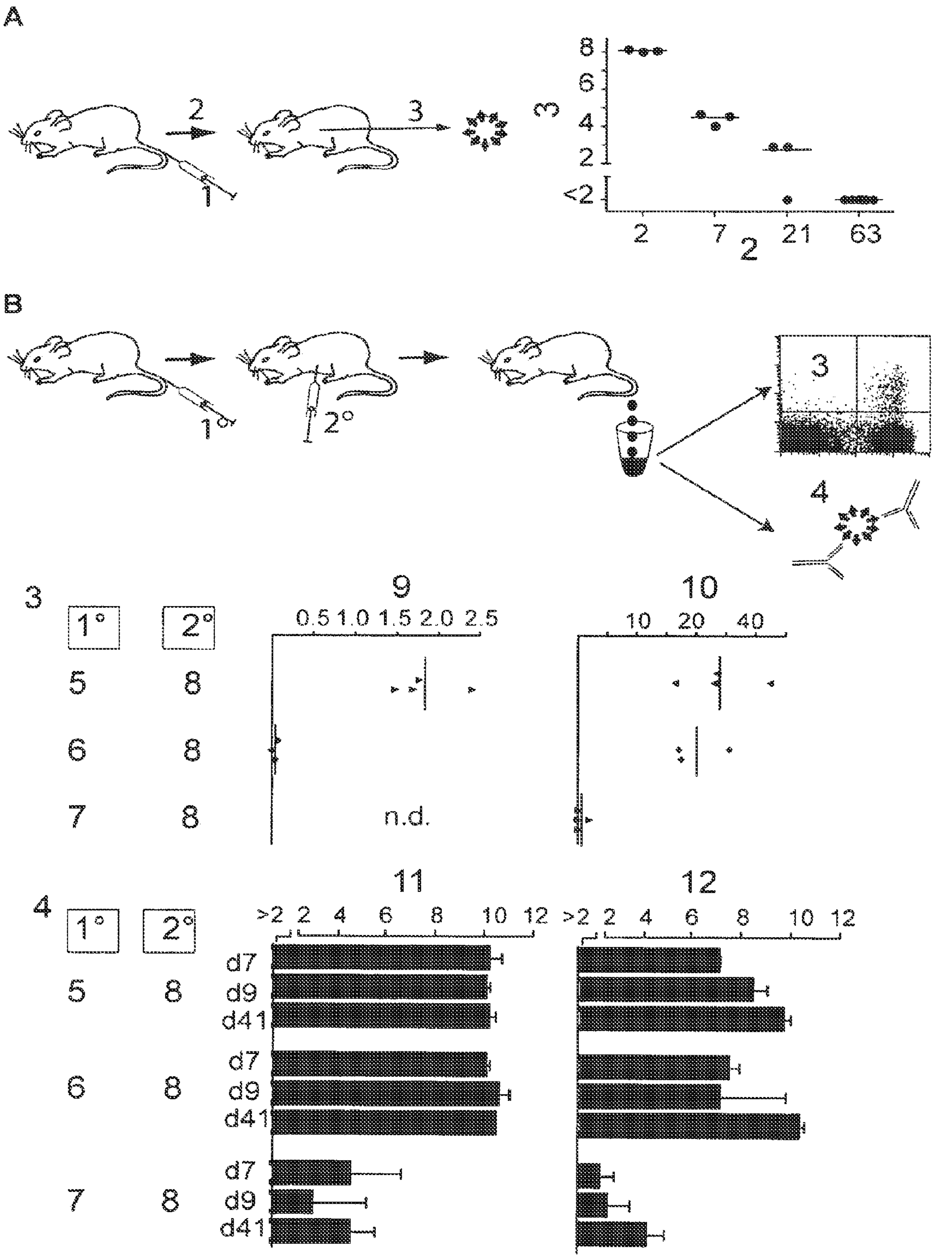

With the same intention, arenavirus vectors can be used to introduce a gene of interest, e.g. foreign nucleic acids, into cells of living animals including men, i.e. as gene therapy, or they can be used to introduce and express a gene product of interest in biotechnological applications. Abolishing replication of arenavirus vectors by deleting from their genome e.g. the Z gene which is required for particle release, or the GP gene which is required for infection of target cells (compare also FIG. 3), the total number of infected cells is limited by the inoculum administered, e.g. to a vaccinee or to a recipient of gene therapy, or accidentally transmitted to personnel involved in medical or biotechnological applications or to animals. Arenavirus disease and immunosuppression in wild type arenavirus infection are both known to result from unchecked viral replication. Therefore, abolishing replication of arenavirus vectors prevents pathogenesis as a result of intentional or accidental transmission of vector particles. In this invention, one important aspect consists in exploiting the above necessity of abolishment of replication in a beneficial way for the purpose of expressing one or more foreign proteins, e.g. antigens of interest: Removal, e.g. structurally by deletion or functionally by mutagenesis, of one or more of the arenavirus genes frees the respective viral promoters for expression of the proteins of choice.

A number of combined advantages characterize the present invention on arenavirus vector strategy: Of note, the retained exquisite immunogenicity of arenavirus vectors—retained despite the inability of arenavirus vectors to spread—comes as a great surprise to immunologists working in the field of arenavirus immunology. A substantial virus and antigen load over a critical period of time is generally considered essential for the unmatched immunogenic properties of arenaviruses. With regard to safety, the virus' (and the vector's) non-cytolytic behavior is a major advantage over most available vector systems, and the same applies to the lack of oncogenic potential of arenaviruses in general. Also, the inability of arenavirus vectors to replicate is of much importance with regard to safety. Very advantageous, particularly for the application as vaccines, is also the high level of resistance of arenavirus vectors to antibody neutralization. This property is inherent to many arenavirus envelopes and allows repeated immunization with the same arenavirus vector resulting in repeated boosting of the immune response. Similarly, pre-existing immunity against arenaviruses is very low or negligible in the human population.

Arenaviruses considered are Old World viruses, for example Lassa virus, Lymphocytic choriomeningitis virus (LCMV), Mobeia virus, Mopes virus, or Ippy virus, or New World viruses, for example Amapari virus, Flexal virus, Guanarito virus, Junin virus, Latino virus, Mechupo virus, Oliveros virus, Paraná virus, Pichinde virus, Pirital virus, Sabiá virus, Tacaribe virus, Tamiemi virus, Bear Canyon virus, or Whitewater Arroyo virus. Preferred are members of the Old World viruses, e.g. Lassa virus or LCMV, in particular LCMV.

Foreign nucleic acids coding for one or more proteins of interest are e.g. messenger RNA-derived sequences or RNA corresponding to a primary gene transcript, leading to expression of the protein of interest when arenavirus particles of the invention carrying this RNA infect a cell. Further foreign nucleic acids considered are those modifying gene expression in cells infected with the arenavirus vector particle, e.g. by RNA interference.

Ribonucleic acids of interest considered to be introduced in engineered arenaviruses of the invention are any sequences coding for protein or modulating host gene expression that can be introduced in an arenavirus vector genome by replacement or fusion to the open reading frame of glycoprotein GP, the matrix protein Z, the nucleoprotein NP, or the polymerase protein L, i.e. that can be transcribed and/or expressed under control of the four arenavirus promoters (5' UTR and 3' UTR of the S segment, and 5' UTR and 3' UTR of the L segment), as well as ribonucleic acids that can be inserted with regulatory elements that can be read by the viral RNA-dependent RNA polymerase, cellular RNA polymerase I, RNA polymerase II or RNA polymerase III, such as duplications of viral promoter sequences that are naturally found in the viral UTRs, the 28S ribosomal RNA promoter, the beta-actin promoter or the 5S ribosomal RNA promoter, respectively. The proteins or nucleic acids are transcribed and/or expressed either by themselves or as read-through by fusion to arenavirus open reading frames and genes, respectively, and/or in combination with one or more, e.g. two, three or four, internal ribosome entry sites. As is demonstrated with genes for GFP and ovalbumin replacing GP, the length of the gene inserted and the properties of the expressed protein are not critical and open the possibility for expression of a large variety of proteins of interest.

Preferred proteins of interest are peptidic or proteinaceous antigens. Peptidic or proteinaceous antigens of the invention may, for example, be selected from the group consisting of (a) proteins or peptides suited to induce or modulate an immune response against infectious diseases; (b) proteins or peptides suited to induce or modulate an immune response against neoplastic diseases, i.e. cancer cells; and (c) proteins or peptides suited to induce or modulate an immune response against allergens. Combinations of antigens, e.g. of antigens derived from one or more infectious organisms or tumors or allergens may be combined to elicit or modulate an immune response protecting or curing more than one infection, type of tumor or allergic disease, respectively.

"Modulating an immune response" as used herein means i) improving, either in quality or quantity, a beneficial immune response of a patient. This is desirable, for example, when enhancing HIV-specific T cell and antibody responses in the context of immunotherapy of an infected individual. The term "modulating an immune response" also refers to ii) the process generally known as desensitization, e.g. desensitization against allergens by suppressing an allergic type of immune response such as the one of the immunoglobulin E isotype, with the attempt of substituting or superimposing a protective immune response or of dampening the pathogenic immune response.

In one specific embodiment of the invention, the antigen is one that is useful for the prevention of infectious disease. Particular examples of antigens or antigenic determinants include the HIV antigens gp 41, gp 120, gag, and pol, non-structural (NS) proteins of Hepatitis C virus, the influenza antigens hemagglutinin and neuraminidase, hepatitis B surface antigen, and circumsporozoite protein of malaria.

Preferably the antigen is selected from respiratory syncytial virus antigens, human immunodeficiency virus antigens, hepatitis C virus antigens, *varicella zoster* virus antigens, *herpes simplex* virus antigens, cytomegalovirus antigens and antigens derive from *mycobacterium tuberculosis.*

The selection of antigens for the composition and method of treatment for cancer would be known to those skilled in the medical art treating such disorders. Representative examples of this type of antigen include the following: HER2/neu (breast cancer), GD2 (neuroblastoma), EGF-R (malignant glioblastoma), CEA (medullary thyroid cancer), CD52 (leukemia), MUC1 (expressed in hematological malignancies), gp100 protein, MELAN-A/MART1 or the product of the tumor suppressor gene WT1.

The selection of antigens for the composition and method of treatment for allergy would be known to those skilled in the medical art treating such disorders. Representative examples of this type of antigen include but are not limited to birch pollen antigen Bet v 1 and at allergen Fel d 1.

The selection of antigens for the composition and method of treatment for obesity would be known to those skilled in the medical art treating such disorders. Representative examples of this type of antigen include but are not limited to ghrelin and gastric inhibitory peptide (GIP).

Design of Arenavirus Vector Genome

Starting out from a wild type arenavirus genome (FIG. 1C), the arenavirus vector genome is designed to retain at least the essential regulatory elements on the 5' and 3' untranslated regions (UTRs) of both segments, and preferentially also the intergenic regions (IGRs). The minimal transacting factors necessary for gene expression in infected cells remain in the vector genome as open reading frames that can be expressed, yet they can be placed differently in the genome and can be placed under control of a different promoter than naturally, or can be expressed from internal ribosome entry sites. At least one of the four viral genes (NP, L, GP, Z) is removed or is functionally inactivated. One or more additional genes or stretches of nucleic acids of interest are inserted into the arenavirus vector genome, placed and oriented to allow their expression in infected cells, either under control of one of the four viral promoters (5' and 3' UTR of the S segment, 5' and 3' UTR of the L segment) or from an internal ribosome entry site or from promoters that can be read by the viral RNA-dependent RNA polymerase, cellular RNA polymerase I, RNA polymerase II or RNA polymerase III. FIG. 1C shows one example where the arenavirus GP open reading frame (ORF) is replaced by either an ovalbumin (OVA) or green fluorescent protein (GFP) ORF.

Generation of a Complementing Cell Line

Figure 2:
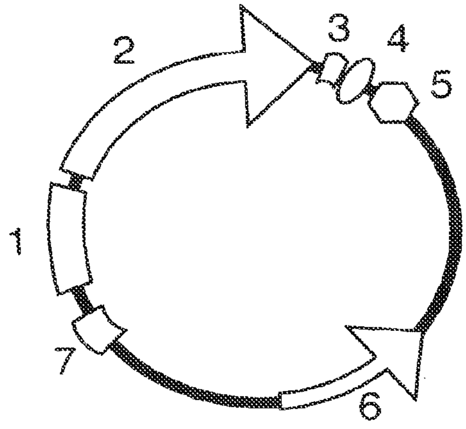
Figure 2:
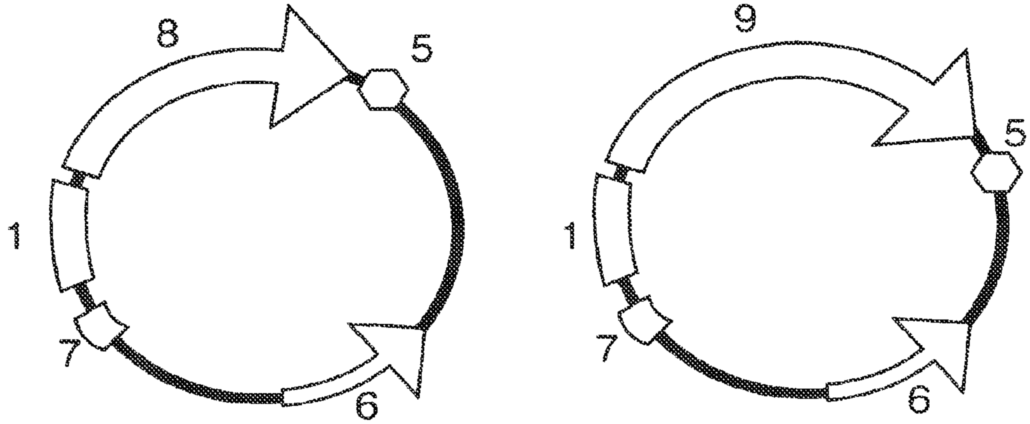
Figure 2:
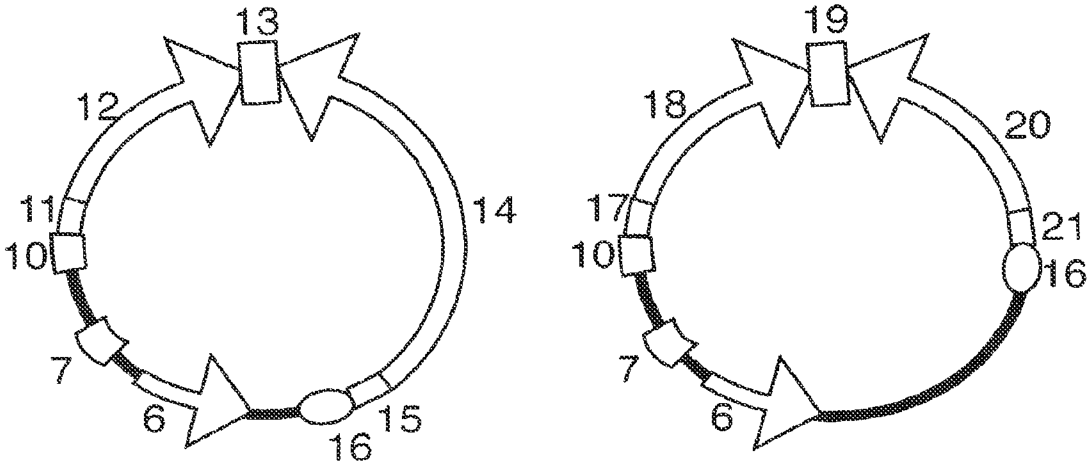

Owing to the "deletion" (referring to either removal or functional inactivation) of one or more of the viral genes in arenavirus vectors (here deletion of the glycoprotein, GP, will be taken as an example), arenavirus vectors must be generated and expanded on cells providing in trans the deleted viral gene(s) e.g. the GP in the present example. Such a complementing cell line, henceforth referred to as C-cells, is generated by transfecting mammalian cell line such as BHK-21, HEK293, VERO or other (here BHK-21 will be taken as an example) with one or more plasmid(s) for expression of the viral gene(s) of interest (complementation plasmid, referred to as C-plasmid). The C-plasmid(s) (for an example see FIG. 2A) express the viral gene(s) deleted in the arenavirus vector to be generated under control of one or more expression cassettes suitable for expression in mammalian cells, e.g. a mammalian polymerase promoter such as the CMV or EF1alpha promoter with a polyadenylation signal. In addition, the complementation plasmid features a mammalian selection marker, e.g. puromycin resistance, under control of an expression cassette suitable for gene expression in mammalian cells, e.g. polymerase II expression cassette as above, or the viral gene transcript(s) are followed by an internal ribosome entry site, such as the one of encephalomyocarditis virus, followed by the mammalian resistance marker. For production in *E. coli*, the plasmid additionally features a bacterial selection marker, such as an ampicillin resistance cassette.

The cells to be used, e.g. BHK-21, HEK293, MC57G or other, are kept in culture and are transfected with the complementation plasmid(s) using any of the commonly used strategies such as calcium-phosphate-, liposome-based protocols or electroporation. A few days later the suitable selection agent, e.g. puromycin, is added in titrated concentrations. Surviving clones are isolated and subcloned following standard procedures, and high-expressing C-cell clones are identified using Western blot or flow cytometry procedures with antibodies directed against the viral protein(s) of interest. As an alternative to the use of stably transfected C-cells transient transfection of normal cells can complement the missing viral gene(s) in each of the steps where C-cells will be used below.

Plasmids for the Recovery Arenavirus Vectors

Plasmids Needed are of Two Types:

i) Two plasmids, referred to as TF-plasmids (for an example see FIG. 2), for expressing intracellularly in C-cells the minimal transacting factors of the arenavirus the vector is derived from e.g. NP and L proteins of LCMV in the present example.

ii) Plasmids, referred to as GS-plasmids (for an example see FIG. 2C), for expressing intracellularly C-cells the arenavirus vector genome segments, e.g. the segments with designed modifications as described in FIG. 1C. TF-plasmids express the NP and L proteins of the respective arenavirus vector under control of en expression cassette suitable for protein expression in mammalian cells, typically e.g. a mammalian polymerase II promoter such as the CMV or EF1alpha promoter, either one of them preferentially in combination with as polyadenylation signal (FIG. 2B). GS-plasmids express the small (S) and the large (L) genome segments of the vector. Typically, polymerase I-driven expression cassettes (FIG. 2C) or T7 bacteriophage RNA polymerase (T7-) driven expression cassettes can be used, the latter preferentially with a 3'-terminal ribozyme for processing of the primary transcript to yield the correct end. In the case of using a T7-based system, expression of T7 in C-cells must be provided by either including in the recovery process an additional expression plasmid, constructed analogously to TF-plasmids, providing, T7, or C-cells are constructed to additionally express T7 in a stable manner.

Recovery of the Arenavirus Vector

First day: C-cells, typically 80% confluent in M6-well plates, are transfected with a mixture of the two TF-plasmids plus the two GS-plasmids. For this one can exploit any of the commonly used strategies such as calcium-phosphate-, liposome-based protocols or electroporation.

3-5 days later: The culture supernatant (arenavirus vector preparation) is harvested, aliquoted and stored at 4° C., −20° C. or −80° C. depending on how long the arenavirus vector should be stored prior to use. Then the arenavirus vector preparation's infectious titer is assessed by an immunofocus assay on C-cells.

Titration of Arenavirus Vector Infectivity

For measuring the infectivity of an arenavirus vector preparation C-cells are used for a typical immunofocus assay following commonly used principles in virology as outlined hereinafter:

C-cell monolayers, typically in M24 well plates, 80% confluent, are infected with 10-fold dilutions of the arenavirus vector preparation for 90 min. Subsequently, the cell layer is overlayed with suitable cell culture medium supplemented with 1% methylcellulose. Two to three days later, depending on the permissiveness of the C-cell line used, the culture supernatant is removed, the cell layer is fixed, typically with ethanol/acetone or with formalin 4%, followed by permeabilization of the cell layer using mild detergents. Subsequently, arenavirus-vector-infected cell foci are identified using mono- or polyclonal antibody preparation(s) against one of the proteins in the arenavirus vector to be tested or against the antigen introduced. Bound antibody is detected using appropriate reagents, such as anti-isotype or anti-species antibodies that are conjugated to a system for visualization such as horse radish peroxidase, followed by a color reaction with suitable chromogens such as o-phenylenediamine. The resulting spots on the plate are counted to calculate the number infectious focus forming units (FFU) per volume of arenavirus vector preparation.

Vaccines and Pharmaceutical Preparations

The invention furthermore relates to vaccines and pharmaceutical preparations comprising the genetically engineered arenaviruses as described hereinbefore. Vaccines and pharmaceutical preparations for other uses are prepared according to standard procedures in the art.

Compositions for enteral administration, such as nasal, buccal, rectal or oral administration, and for parenteral administration, such as intravenous, intramuscular, intradermal or subcutaneous administration, to warm-blooded animals, especially humans, are preferred. Particularly preferred are compositions for parenteral administration. The compositions comprise the genetically engineered arenaviruses alone or, preferably, together with a pharmaceutically acceptable carrier. The dosage of the active ingredient depends upon the type of vaccination and the disease to be treated and upon the species, its age, weight, and individual condition, the individual pharmacokinetic data, and the mode of administration.

The pharmaceutical compositions comprise from about $10^3$ to about $10^{11}$ focus forming units of the genetically engineered arenaviruses. Unit dose forms for parenteral administration are, for example, ampoules or vials, e.g. vials containing from about $10^3$ to $10^{10}$ focus forming units or $10^5$ to $10^{15}$ physical particles of genetically engineered arenaviruses.

Preference is given to the use of suspensions or dispersions of genetically engineered arenaviruses, especially isotonic aqueous dispersions or suspensions. The pharmaceutical compositions may be sterilized and/or may comprise excipients, e.g. preservatives, stabilizers, wetting agents and/or emulsifiers, solubilizers, salts for regulating osmotic pressure and/or buffers and are prepared in a manner known per se, for example by means of conventional dispersing and suspending processes. The said dispersions or suspensions may comprise viscosity-regulating agents. The suspensions or dispersions are kept at temperatures around 2-4° C., or preferentially for longer storage may be frozen and then thawed shortly before use.

The invention relates also to processes and to the use of genetically engineered arenaviruses for the manufacture of vaccines in the form of pharmaceutical preparations, which comprise genetically engineered arenaviruses as active ingredient. The pharmaceutical compositions of the present invention are prepared in a manner known per se, for example by means of conventional mixing and/or dispersing processes.

Administration to Vaccinee and to Gene Therapy Recipient

The invention furthermore relates to methods of vaccination and gene therapy using the genetically engineered arenaviruses as described hereinbefore.

Arenavirus vectors are administered for improving the quality of live, including but not limited to vaccination, immunotherapy and gene therapy in order to prevent, treat or improve i) infections including but not limited to those caused by viruses such as human immunodeficiency virus (HIV), hepatitis B virus (HBV), hepatitis C virus (HCV), influenza viruses, and respiratory syncytial virus (RSV), bacteria such as mycobacteria, *haemophilus* spp., and *pneumococcus* spp., parasites such as plasmodia, amebia, and philaria, and prions such as the infectious agents causing classical and variant Creutzteldt-Jakob disease and mad cow disease;

ii) autoimmune diseases including but not limited to type I diabetes, multiple sclerosis, rheumatoid arthritis, lupus erythematosus, and psoriasis;

iii) neoplastic diseases including but not limited to melanoma, prostate carcinoma, breast carcinoma, lung carcinoma, and neuroblastoma;

iv) metabolic diseases including but not limited to type II diabetes, obesity, and gout;

v) degenerative diseases including but not limited to Alzheimer's disease and Parkinson's disease;

vi) inherited diseases inducting but not limited to Huntington's disease, severe combined immunodeficiency, and lipid storage diseases; and vii) substance dependence including but not limited to tobacco and alcohol abuse.

In particular the invention relates to a method of preventing infections by viruses, bacteria, parasites and prions comprising administering a vaccine comprising genetically engineered arenaviruses to a patient in need thereof, and likewise to a method of preventing neoplastic diseases and degenerative diseases as listed hereinbefore.

Furthermore the invention relates to a method of treating infections by viruses, bacteria, parasites and prions, autoimmune diseases, neoplastic diseases, metabolic diseases, degenerative diseases, inherited diseases, or substance dependence comprising administering a pharmaceutical preparation comprising genetically engineered arenaviruses to a patient in need thereof.

Figure 5:
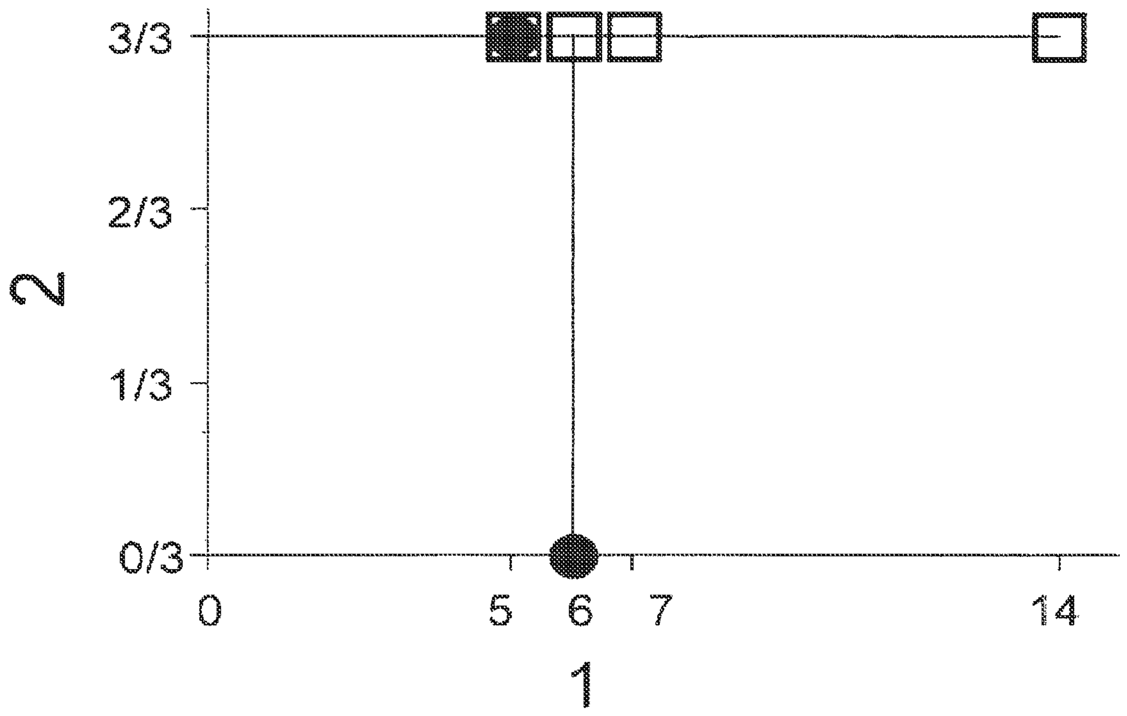

Arenavirus vectors are administered to a vaccinee either by one or by multiple ones of the available routes including but not limited to intramuscular, intradermal, subcutaneous, peroral, intranasal, or intravenous routes, e.g. as in the experiment outlined in FIG. 3A. This results in infection of cells, amplification of the viral genome segments in these very same initially infected cells, e.g. after intravenous inoculation. This comprises dendritic cells of the spleen that can trigger T cell responses. Owing to the inability of the arenavirus vector to replicate in cells of a vaccines, lacking the complementing viral protein present in C-cells, the levels of arenavirus vector RNA decline rapidly over time and the viral genome approaches its extinction within days after inoculation of the arenavirus vector (FIG. 3A). Owing to the lack of arenavirus vector replication and persistence, and in contrast to infection with the same dose of wild type virus, arenavirus vector immunization does not cause immunosuppression (FIG. 3B) or disease (FIG. 5). This is tested in mice infected either with wild type LCMV or with an LCMV-based vector expressing OVA instead of LCMV-GP (rLCMV/OVA; compare FIG. 1C). Subsequent infection with vesicular stomatitis virus elicited a normal CD8 T cell and antibody response in animals previously immunized with rLCMV/OVA, but was suppressed in animals previously infected with wild type LCMV. Similarly, wild type LCMV elicited lethal choriomeningitis in mice when administered intracranially, but rLCMV/OVA did not elicit any clinically detectable signs of illness (FIG. 5).

Figure 4:
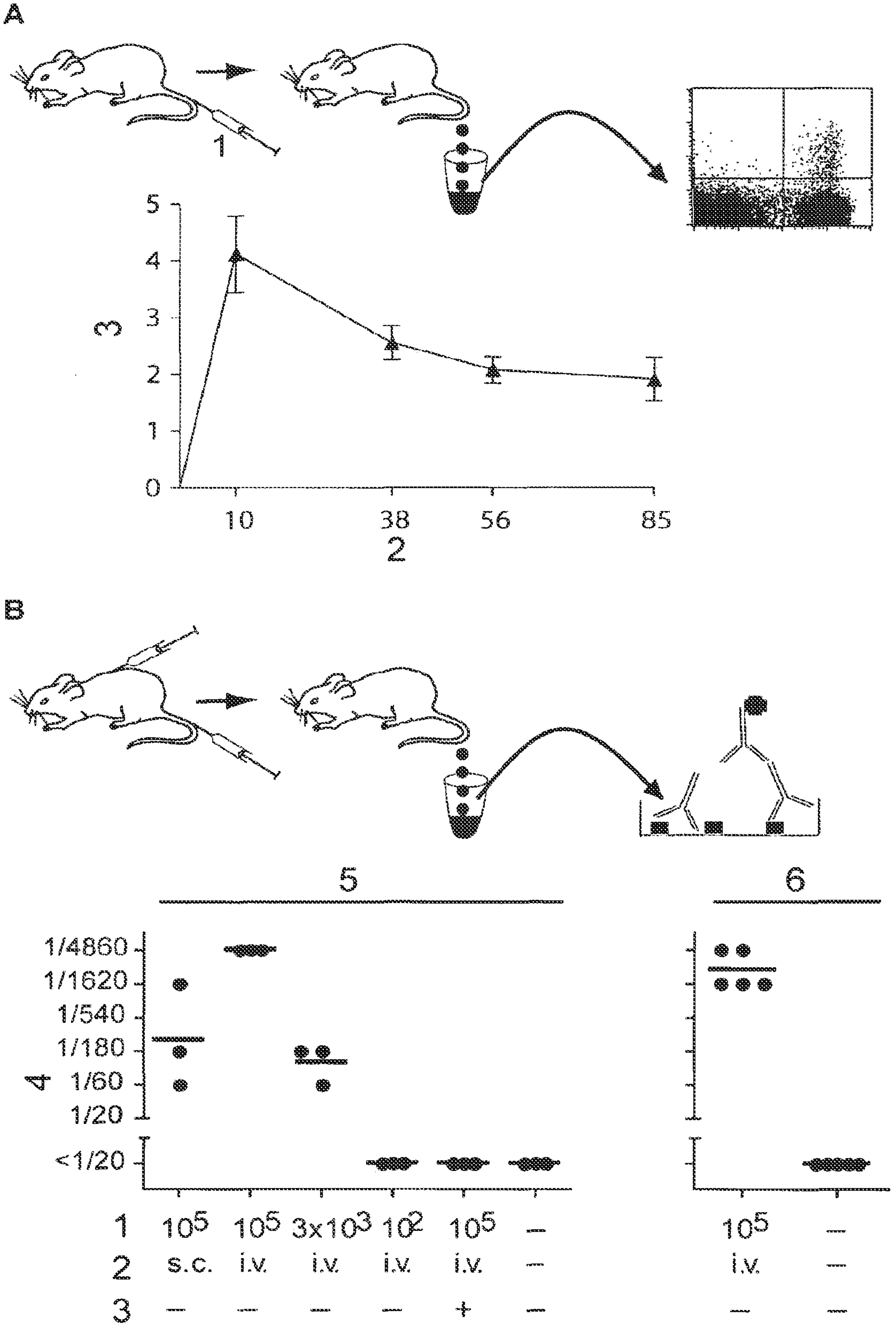
Figure 6:
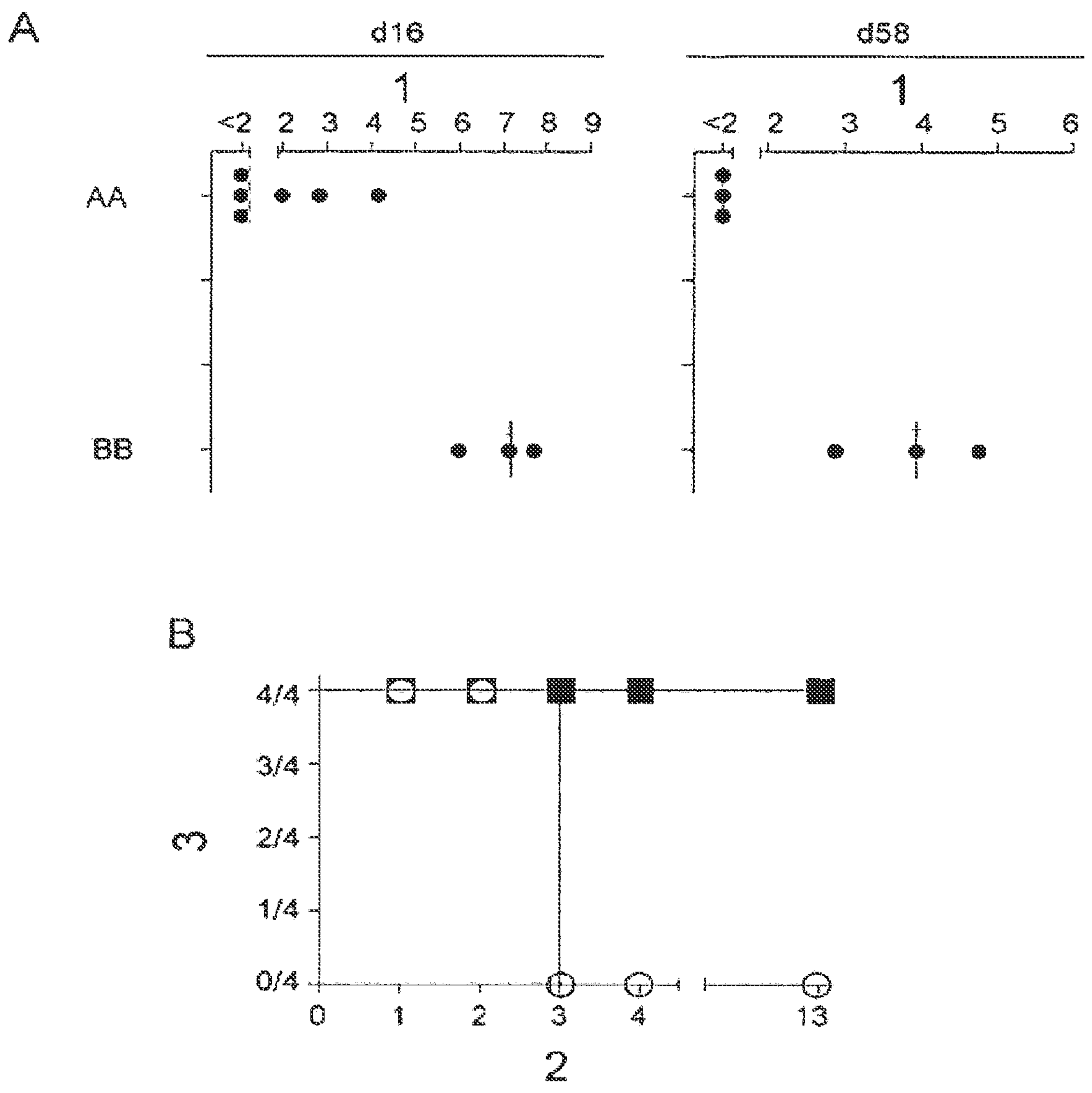

Despite its transient nature, expression of the antigen of interest does, however, evoke a strong and long-lasting T cell response (FIG. 4A) and evokes high titers of specific antibodies (FIG. 4B). This response is dose-dependent but even small doses are efficient (FIG. 4B). The protective capacity of T cell responses elicited by LCMV-based vaccine vectors is tested in mice. Immunization with rLCMV/OVA protected against infectious challenge with recombinant *Listeria monocytogenes* expressing OVA (rLM/OVA). This was evident in strongly reduced or undetectable rLM/OVA titers in the spleen of vaccinated animals (FIG. 6A). Induction of antibody-mediated protection by LCMV vector is tested in mice lacking the type I interferon receptor. The mice are highly susceptible to vesicular stomatitis virus (VSV), with a 50% lethal dose ($LD_{50}$) in the range of 50 PFU. For immunization against VSV, a LCMV vector was used that expresses an antigenic but non-functional variant of the vesicular stomatitis virus envelope protein G (modified by insertion of a foreign peptide sequence in its ectodomain). Immunized mice survived a challenge infection with $2\times10^8$ PFU VSV (i.e. >10,000-fold $LD_{50}$), whereas unimmunized control mice developed terminal myeloencephalitis within two to three days after VSV challenge (FIG. 6). Of note, though, inactivation of the arenavirus vector genome by UV irradiation abrogated its immunogenicity, demonstrating that replication and gene expression of the viral vector in infected cells is essential for its efficacy as a vaccine. Additionally, T cell and antibody responses can be enhanced by repeated applications of the same (homologous) or different (heterologous) arenavirus vectors, i.e. in the form of booster immunization. In homologous prime-boost regimens, the virtual absence of neutralizing antibody induction renders booster immunizations particularly efficient.

When used for gene therapy, arenavirus vectors can be applied systemically, e.g. intravenously, or topically, e.g. by stereotactic injection using appropriate equipment, for targeting and delivery to specific tissues where the antigen of interest should be expressed. Owing to its non-cytolytic nature, the arenavirus vector does not harm the cell it infects and can functionally substitute for a gene of interest.

As an alternative way of exploiting arenavirus vectors for treatment of multicellular organisms, complementing (C-cells) or non-complementing (normal) cells are implanted into a recipients body encapsulated by biocompatible materials preventing immune rejection by the recipient yet allowing for the constant release of infectious (implantation of infectious C-cells) or non-infectious (implantation of infected normal cells) particles or of proteins and/or ribonucleic acids from the encapsulated cells across the capsule into the recipients tissue.

Expression of a Protein of Interest in a Cell Culture

The invention furthermore relates to expression of a protein of interest in a cell culture wherein the cell culture is infected with genetically engineered arenaviruses. When used for expression of a protein or stretch of nucleic adds of interest, e.g. an antigen of interest, in cultured cells, the following two procedures are envisaged:

i) The cell type of interest is infected with the arenavirus vector preparation at a multiplicity of infection (MOI) of one or more, e.g. two, three or four, resulting in production of the protein of interest in all cells already shortly after infection.

ii) Alternatively, a lower MOI can be used and individual cell clones can be selected for their level of virally driven protein expression. Subsequently individual clones can be expended infinitely owing to the non-cytolytic nature of arenavirus vectors. Irrespective of the approach, the protein (s) of interest can subsequently be collected (and purified) either from the culture supernatant or from the cells themselves, depending on the properties of the protein(s) produced.

However, the invention is not limited to these two strategies, and other ways of driving expression of proteins or nucleic acids of interest using genetically engineered arenaviruses as vectors may be considered.

The invention claimed is:

1. An infectious arenavirus particle comprising a genome wherein i) one or more of the four arenavirus open reading frames coding for the glycoprotein (GP), nucleoprotein (NP), matrix protein Z and RNA-dependent RNA polymerase L are removed or mutated such that the infectious arenavirus particle is unable to produce further infectious progeny particles in normal, not genetically engineered cells but still allowing gene expression in arenavirus vector-infected cells; and ii) the genome comprises a foreign ribonucleic acid coding for one or more tumor antigens.

2. The arenavirus particle according to claim 1 wherein the arenavirus open reading frame coding for glycoprotein (GP) is removed or mutated.

3. The arenavirus particle according to claim 1 wherein the genome comprises additional nucleic acids modulating host gene expression.

4. The arenavirus particle according to claim 1 wherein the arenavirus is lymphocytic choriomeningitis virus (LCMV).

5. A pharmaceutical preparation comprising an arenavirus particle according to claim 1.

6. The arenavirus particle according to claim 1, wherein an internal ribosome entry site is introduced into the viral genome.

7. The infectious arenavirus particle of claim 1 or claim 2, wherein the open reading frames for the NP protein and the RNA-dependent RNA polymerase L of the arenavirus are intact.

8. The arenavirus particle according to claim 1, wherein the foreign ribonucleic acid is expressed under control of one or more of the four arenavirus promoters 5' UTR and 3' UTR of the S segment, and 5' UTR and 3' UTR of the L segment, and/or under control of regulatory elements that can be read by the viral RNA-dependent RNA polymerase, cellular RNA polymerase I, RNA polymerase II or RNA polymerase III, expressed either by themselves or as read-through by fusion to arenavirus protein open reading frames.

9. The arenavirus particle according to claim 1, wherein the tumor antigen is HER2/neu (breast cancer), GD2 (neuroblastoma), EGF-R (malignant glioblastoma), CEA (medullary thyroid cancer), CD52 (leukemia), MUC1 (expressed in hematological malignancies), gp100 protein, MELAN-A/MART1, or the product of the tumor suppressor gene WT1.

10. The arenavirus particle according to claim 1, wherein the genome is engineered to have the ability to amplify and express its genetic information in the arenavirus vector infected cells.

11. A method of expressing a tumor antigen in a cell culture wherein the cell culture is infected with an arenavirus particle according to claim 1.

* * * * *